US006284750B1

(12) United States Patent
Gubernick et al.

(10) Patent No.: US 6,284,750 B1
(45) Date of Patent: Sep. 4, 2001

(54) α-HYDROXYACID ESTERS OF DHEA USEFUL AGAINST SKIN DISORDERS

(75) Inventors: Joseph Gubernick, New York; Daniel H. Maes, Huntington, both of NY (US)

(73) Assignee: Estee Lauder Inc., New York, NY (US)

( * ) Notice: Subject to any disclaimer, the term of this patent is extended or adjusted under 35 U.S.C. 154(b) by 0 days.

(21) Appl. No.: 09/491,710

(22) Filed: Jan. 26, 2000

Related U.S. Application Data

(63) Continuation of application No. 09/008,444, filed on Jan. 16, 1998, now Pat. No. 6,025,347, which is a continuation of application No. 08/527,145, filed on Sep. 12, 1995, now Pat. No. 5,736,537.

(51) Int. Cl.[7] .............................. C07J 1/00; A61K 31/565
(52) U.S. Cl. .................. 514/178; 514/844; 514/859; 514/861; 514/863; 552/636
(58) Field of Search .................... 514/178, 844, 514/859, 861, 863; 552/636

(56) References Cited

U.S. PATENT DOCUMENTS

| | | |
|---|---|---|
| 3,879,537 | 4/1975 | Van Scott et al. . |
| 3,920,835 | 11/1975 | Van Scott et al. . |
| 3,984,566 | 10/1976 | Van Scott et al. . |
| 3,988,470 | 10/1976 | Van Scott et al. . |
| 4,105,782 | 8/1978 | Yu et al. . |
| 4,105,783 | 8/1978 | Yu et al. . |
| 4,194,007 | 3/1980 | Van Scott et al. . |
| 4,197,316 | 4/1980 | Yu et al. . |
| 4,234,599 | 11/1980 | Van Scott et al. . |
| 4,246,261 | 1/1981 | Van Scott et al. . |
| 4,363,815 | 12/1982 | Yu et al. . |
| 4,380,549 | 4/1983 | Van Scott et al. . |
| 4,496,556 | 1/1985 | Orentriech . |
| 4,542,129 | 9/1985 | Orentreich . |
| 4,628,052 | 12/1986 | Peat . |
| 4,898,694 | 2/1990 | Schwartz et al. . |
| 4,920,115 | 4/1990 | Nestler et al. . |
| 4,956,355 | 9/1990 | Prendergast . |
| 5,001,119 | 3/1991 | Schwartz et al. . |
| 5,028,631 | 7/1991 | Schwartz et al. . |
| 5,077,284 | 12/1991 | Loria et al. . |
| 5,091,171 | 2/1992 | Yu et al. . |
| 5,110,810 | 5/1992 | Eich et al. . |
| 5,162,198 | 11/1992 | Eich et al. . |
| 5,206,008 | 4/1993 | Loria et al. . |
| 5,227,907 | 7/1993 | Loria et al. . |
| 5,232,917 | 8/1993 | Bolger et al. . |
| 5,254,343 | 10/1993 | Parah et al. . |
| 5,262,407 | 11/1993 | Leveque et al. . |
| 5,387,583 | 2/1995 | Loria et al. . |
| 5,407,684 | 4/1995 | Loria et al. . |
| 5,736,537 | 4/1998 | Gubernick et al. . |

FOREIGN PATENT DOCUMENTS

| | | |
|---|---|---|
| 67494/87 | 1/1986 | (AU) . |
| 608824 | 4/1988 | (AU) . |
| 2147309 | 3/1973 | (DE) . |
| 0 133 995 | 8/1984 | (EP) . |
| 0 210 665 | 2/1987 | (EP) . |
| 0 282 156 | 9/1988 | (EP) . |
| 2 208 473 | 4/1989 | (GB) . |
| 60-161912 | 8/1985 | (JP) . |
| WO91/04030 | 4/1991 | (WO) . |
| WO93/10756 | 6/1993 | (WO) . |
| WO93/21771 | 11/1993 | (WO) . |
| WO94/17823 | 8/1994 | (WO) . |
| WO94/20111 | 9/1994 | (WO) . |

OTHER PUBLICATIONS

Bellman, et al., "In Vitro Studies on Enzymatic Cleavage of Steroid Esters in the Female Organism" (1976) *Acta Endocrinologica 81*, 839–53.

Morrison, M.T. and Boyd, R. N, "Organic Chemistry," Third Edition, Allyn and Bacon, Inc., Boston, pp. 672–673, 1973.

Adolf and Swetly, 1979, "Glucocorticoid hormones inhibit DNA synthesis and enhance interferon production in a human lymphoid cell line", *Nature 282*: 736–738.

Culpepper and Lee, 1987, "Glucocorticoid Regulation of Lymphokine Production by Murine T Lymphocytes", *Lymphokines 13*: 275–289.

Daynes et al., 1990, "Regulation of murine lymphokine production in vivo II. Dehydroepiandrosterone is a natural enhancer of interleukin 2 synthesis by helper T cells" European *Journal of Immunology 20*: 793–802.

Daynes et al., 1990, "Regulation of Murine Lymphokine Production In Vivo; III. The Lymphoid Tissue Microenvironment Exerts Regulatory Influences over T Helper Cell Function" *J. Experimental Medicine 171*: 979–996.

Daynes and Araneo, 1989, "Contrasting effects of glucocorticoids on the capacity of T cells to produce the growth factors interleukin 2 and interleukin 4", *European Journal of Immunology 19*: 2319–2325.

(List continued on next page.)

*Primary Examiner*—Barbara P. Badio
(74) *Attorney, Agent, or Firm*—Pennie & Edmonds LLP

(57) ABSTRACT

Disclosed are compounds of formula II:

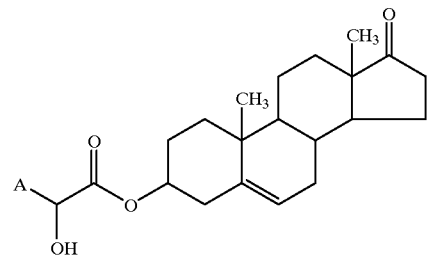

wherein A is as defined by the specification. Also disclosed are compositions containing the esters and methods for their use in the regulation of skin atrophy and in the treatment of skin disorders such as dry skin, dandruff, acne and eczema.

12 Claims, No Drawings

OTHER PUBLICATIONS

Lobo et al., 1981, "Dehydroepiandrosterone Sulfate as an Indicator of Adrenal Androgen Function", *Obstetrics and Gynecology* 57: 69–73.

Loria et al., 1988, "Protection Against Acute Lethal Viral Infections With the Native Steroid Dehydroepiandrosterone (DHEA)", *Journal of Medical Virology 26:* 301–314.

Loria and Padgett, 1992, "Mobilization of Cutaneous Immunity for Systemic Protection Against Infections", *Annals New York Academy of Sciences 650:* 363–366.

Orentreich et al., 1984," Age Changes and Sex Differences in Serum Dehydroepiandrosterone Sulfate Concentrations throughout Adulthood", *J. Clin. Endocrinol. Metab.* 59(3): 551.

Regelson et al., 1988, "Hormonal Intervention: 'Buffer Hormones' or 'State Dependency' The Role of Dehydroepiandrosterone (DHEA), Thyroid Hormone, Estrogen and Hypophysectomy in Aging", *Annals of the New York Academy of Sciences 521:* 260–73.

Solomons, Organic Chemistry, 3rd edition, pp. 794–795, 1984.

R.T. Morrison et al., *Organic Chemistry* 602–603 (3d ed. 1973).

R.T. Morrison et al., *Organic Chemistry* 672–673 (3d ed. 1973).

L.G. Wade, Jr. *Organic Chemistry* 2d Edition, Prentice Hall, Englewood Cliffs, New Jersey (1991).

L.G. Wade, Jr. *Organic Chemistry* 2d Edition, Prentice Hall, Englewood Cliffs, New Jersey, p. 910, (1991).

α-HYDROXYACID ESTERS OF DHEA USEFUL AGAINST SKIN DISORDERS

This is a continuation of application Ser. No. 09/008,444, filed Jan. 16, 1998, now U.S. Pat. No. 6,025,347, which is a continuation of application Ser. No. 08/527,145, filed Sep. 12, 1995, now U.S. Pat. No. 5,736,537.

1. FIELD OF THE INVENTION

This invention relates to novel steroid esters useful for regulating skin atrophy and other skin maladies, to pharmaceutical or cosmetic compositions containing such steroid esters and to methods for their use.

2. BACKGROUND OF THE INVENTION

Dehydroepiandrosterone (DHEA) having the formula:

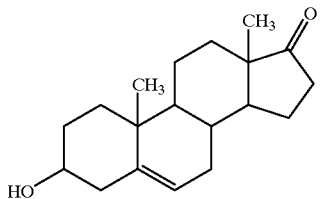

I and its sulfate ester (DHEAS) are secretory products of the human adrenal cortex. Both DHEA and DHEAS circulate in the blood stream at levels that vary with age in adult men and women. For example, blood plasma levels of DHEAS have been show to decrease fairly rapidly from a high level in newborns, then peak again in early advancing age (see, Orentreich, et al., J. Clin. Endocrinol. Metab., 59(3), 551 (1984).

DHEA has been used to treat a variety of ailments. U.S. Pat. No. 4,628,052 to Peat teaches the use of DHEA and other steroids for treating arthritis and non-specific joint pain. International Publication WO 93/21771 to Daynes, et al. teaches the use of DHEA to reduce abnormally elevated interleukin 6 levels to treat individuals with rheumatoid arthritis, bacterial meningitis, alcoholic liver cirrhosis, AIDS, and other pathologic conditions, as well as to treat burn victims and surgery patients.

DHEA has also been used to alleviate skin ailments. U.S. Pat. No. 4,496,556 to Orentreich teaches the use of DHEA and fatty acid esters thereof, including DHEA acetate, DHEA valerate and DHEA enanthate to treat dry skin. Japanese Patent Application 60-161912 to Ogawa et al., teaches cosmetic compositions containing a water-soluble DHEA salt to treat chapped skin. German patent No. DE 2147309 teaches the use of DHEA to treat psoriasis.

Non-steroid molecules, such as hydroxybenzoic acids and α-hydroxycarboxylic acids have also been used to treat skin conditions. α-Hydroxycarboxylic acids have been used to treat ichthyosis, hyperkeratoses, dandruff and acne (see, U.S. Pat. Nos. 3,879,537 to Van Scott et al.; 3,920,835, 3,988,470, and 4,234,599 to Van Scott et al.; 3,984,566 to Van Scott et al.; and 4,105,782 to Yu et al.; respectively). α-Hydroxycarboxylic acids have also been used to treat dry skin (see, U.S. Pat. Nos. 4,105,783 to Yu et al.; 4,194,007 to Van Scott et al.; 4,197,316 to Yu et al.; 4,380,549 to Van Scott et al.; 4,363,815 to Yu et al. and 4,091,171 to Yu et al. α-Hydroxycarboxylic acids have also been used to enhance the antiinflammatory action of corticosteroids (see, U.S. Pat. No. 4,246,261 to Van Scott et al.). U.S. Pat. No. 5,254,343 to Parah et el. discloses the use of salts of α-hydroxyacids in conjunction with steroids to minimize cutaneous atrophy, a side-effect of steroid application to the skin.

One of the drawbacks of using α-hydroxyacids for treating skin ailments of a patient is that at high concentrations, α-hydroxyacids are known to remove the outer layer of skin by effectively burning the skin off the patient. Such treatments are known in the art as "chemical peels." However, when improperly monitored, chemical peeling of the outer layer of skin using α-hydroxyacids can lead to inflammation, infection and scarring. Thus there is a need for a composition capable of providing the skin-healing benefits of α-hydroxyacids while avoiding the drawbacks such as those described above.

Salicylic acid has also been used to treat conditions of the skin. International Publication No. WO 93/10756, published Jun. 10, 1993 to Blank teaches the use of salicylic acid to regulate wrinkles and/or atrophy in mammalian skin. U.S. Pat. No. 5,262,407 to Leveque et al. teaches the use of $C_1$–$C_{18}$ alkanoyl 5-acylsalicylic acids to treat aging skin.

One of the drawbacks associated with the use of DHEA in the treatment of skin is that the increased sebum production resulting from such treatment is accompanied by or associated with the formation of acne-like skin lesions in people who have a genetic tendency for acne. U.S. Pat. No. 4,542,129 to Orentreich teaches the use of a mixture of DHEA and a keratolytic agent, such as a hydroxybenzoic acid or an α-hydroxycarboxylic acid, to treat dry skin while deterring acne formation.

Thus, there is a need for a composition with skin healing properties of DHEA but that does not have the DHEA disadvantages. Similarly, there is a need for compounds having the advantageous properties of α-hydroxycarboxylic acids that can function more effectively with steroid compounds and without the deleterious effects of conventional α-hydroxyacids.

Moreover, when compositions comprising more than one agent useful for treating skin are intended to be formulated, solvents or vehicles which successfully dissolve or suspend one of the necessary agents may be completely ineffective in dissolving or suspending the other(s), and vice versa. This can result in an excessive amount of time, energy and manpower required for determining the proper formulation solvents or vehicles. Thus, there remains a need for such a composition which can be more efficiently formulated.

It is an object of the present invention to provide novel compounds with enhanced skin-healing properties. It is a further object to provide compounds which have the advantages of DHEA and keratolytic agents without the above-mentioned biological disadvantages or formulation problems.

3. SUMMARY OF THE INVENTION

The present invention provides novel steroid esters useful in regulating skin atrophy and other skin maladies, compositions containing the steroid esters and methods for their use.

Thus, the invention encompasses a steroid ester having the formula:

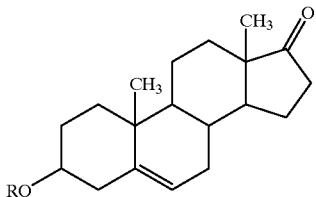

and pharmaceutically or cosmetically acceptable salts thereof, wherein,

R is A—CH(OH)—C(O)— or (HO)C$_6$H$_4$C(O)—; and

A is hydrogen or a C$_1$–C$_{22}$ alkyl or alkenyl group, said C$_1$–C$_{22}$ alkyl or alkenyl group being optionally substituted with one or more C$_1$–C$_4$ alkyl groups, phenyls, halogens or hydroxyl groups, said phenyl being optionally substituted with one or more halogens, hydroxyl groups or methoxyl group, useful in regulating skin atrophy.

In a preferred embodiment of the invention, R is selected from the group consisting of 2-hydroxyethanoyl; 2-hydroxypropanoyl; 2-methyl-2-hydroxypropanoyl; 2-hydroxybutanoyl; 2-hydroxypentanoyl; 2-hydroxynonanoyl; 2-hydroxydecanoyl; 2-hydroxyoctanoyl; 2-hydroxydodecanoyl; 2-hydroxytetradecanoyl; 2-hydroxyhexadecanoyl; 2-hydroxyoctadecanoyl; 2-hydroxyeicosanoyl; 2-hydroxyphenyl-2-hydroxyethanoyl; 2,2-diphenyl-2-hydroxyethanoyl; 3-phenyl-2-hydroxypropanoyl; 2-phenyl-2-methyl-2-hydroxyethanoyl; 2-(4'-chlorophenyl)-2-hydroxyethanoyl; 2-(4'-hydroxy-3'methoxyphenyl)-2-hydroxyethanoyl; 3-(2'-hydroxyphenyl)-2-hydroxypropanoyl; 3-(4'-hydroxyphenyl)-2-hydroxypropanoyl; 2-(3',4'-dihydroxyphenyl)-2-hydroxyethanoyl; and salicylyl. A preferred compound of this invention is

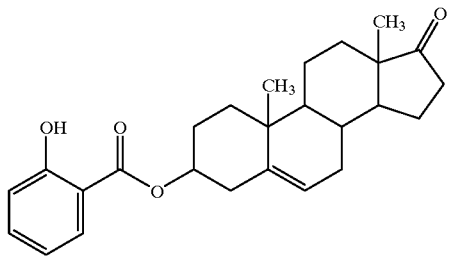

and pharmaceutically or cosmetically acceptable salts thereof.

In further embodiments, the invention encompasses cosmetic or pharmaceutical compositions containing one or more compounds of formula II or a pharmaceutically or cosmetically acceptable salt thereof, and a pharmaceutically or cosmetically acceptable carrier or excipient.

In a still further embodiment, the invention encompasses methods for regulating skin atrophy comprising administering to a subject a safe and effective amount of one or more compounds of formula II, or a pharmaceutically or cosmetically acceptable salt thereof, as described above.

In yet another embodiment, the invention encompasses methods for regulating skin atrophy comprising administering to a subject a safe and effective amount of a composition comprising one or more compounds of formula II, or a pharmaceutically or cosmetically acceptable salt thereof and a pharmaceutically or cosmetically acceptable carrier or excipient.

In yet another embodiment, the invention encompasses methods for treating disorders including but not limited to dry skin, dandruff, acne, keratoses, psoriasis, eczema, pruritis, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers.

The compounds of the present invention surprisingly demonstrate pharmaceutical activity or cosmetic effects against skin disorders heretofore not achieved by DHEA itself or by the combination of DHEA and keratolytic agents.

The present invention may be understood more fully by reference to the detailed description and illustrative examples which are intended to exemplify non-limiting embodiments of the invention.

4. DETAILED DESCRIPTION OF THE INVENTION

1. Definitions

As used herein, "skin atrophy" means the thinning and/or general degradation of the dermis often characterized by a decrease in collagen and/or elastin as well as decreased number, size and doubling potential of fibroblast cells. Skin atrophy is a natural result of aging. Skin atrophy may be caused by either intrinsic or extrinsic factors such as natural chronoaging, photodamage, burns, or chemical damage. Skin atrophy is often an undesirable side effect resulting from treatment with corticosteroids.

As used herein, "regulating skin atrophy" means preventing, retarding, arresting, treating or reversing the process of atrophy in mammalian skin.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound, compounds or composition employed, the particular pharmaceutically-acceptable carrier utilized, and like factors within the knowledge and expertise of the attending physician or health care provider.

As used herein, "steroid ester" means any compound of formula II wherein the hydroxyl group of DHEA is covalently bonded to a hydroxy-substituted acyl or benzoyl moiety, forming an ester bond therewith.

As used herein, "cosmetic" means a formulation to be applied to the skin which improves the texture or appearance thereof, without necessarily rendering a benefit or an effect of treating or preventing an abnormal biological condition or a disease.

As used herein, "pharmaceutical" means a formulation to be applied to the skin which renders a benefit or an effect of treating or preventing an abnormal biological condition or a disease.

As used herein, "eq." means a molar equivalent relative to the limiting reagent in the reaction mixture.

4.2. Synthesis

The compounds of the present invention can be synthesized in accordance with standard organic chemical techniques using readily/commercially available starting materials. Examples of the synthesis of such compounds are described below in Scheme 1.

Scheme 1

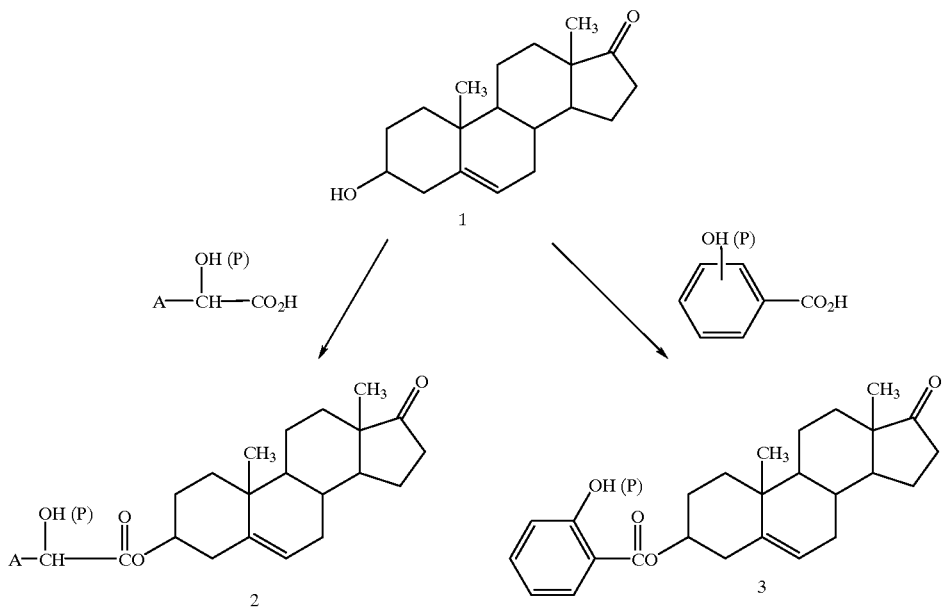

Steroid alcohol 1 can be obtained commercially from the Aldrich Chemical Co., isolated from the human adrenal cortex, or synthesized by conventional organic synthesis.

The steroid alcohol 1 may be esterified with either an α-hydroxycarboxylic acid of the formula A—CH(OH)CO$_2$H or a hydroxybenzoic acid of the formula (HO)C$_6$H$_4$CO$_2$H, wherein A is hydrogen or a C$_1$–C$_{22}$ alkyl or alkenyl group optionally substituted with one or more C$_1$–C$_4$ alkyl groups, phenyls, halogens or hydroxyl groups, said phenyl being optionally substituted with one or more halogens, hydroxyl groups or methoxyl groups. Optionally, the steroid alcohol 1 may be esterified with a protected α-hydroxy acid having the formula A—CH(OP)CO$_2$H or a protected hydroxybenzoic acid of the formula (PO)C$_6$H$_4$CO$_2$H, wherein A is defined as above and P is a suitable protecting group which allows the steroid hydroxyl to participate in an esterification reaction with the carboxyl group of either protected or unprotected carboxylic acid without interference from the unprotected hydroxyl group. It is to be understood that the (HO) or (PO) moiety of the compound of formula 3 is "ortho" relative to the carboxyl group. Suitable protecting groups are those which may be removed subsequent to the esterification reaction with steroid alcohol 1 without resulting in cleavage of the newly formed ester bond. Examples of such protecting groups may be found in T. D. Greene, *Protecting Groups in Organic Synthesis*, John Wiley & Sons, New York, 1981. Where A is optionally substituted with one or more hydroxyl groups, one or more of those hydroxyl groups may be optionally protected with a suitable protecting group as defined above.

Steroid alcohol 1 is heated with either the protected or unprotected carboxylic acids, optionally in the presence of an acid catalyst, to obtain esters 2 or 3, respectively. Such an esterification proceeds with concomitant loss of water. Suitable acid catalysts which can be used include, but are not limited to hydrochloric acid, sulfuric acid, p-toluene sulfonic acid, methanesulfonic acid and other such acid catalysts known to those skilled in the art. In this case, the protecting group (P) should be stable to acidic conditions.

Alternatively, the protected or unprotected carboxylic acids may be converted to their respective alkyl ester derivatives, preferably methyl ester derivatives, prior to esterification via means recited above. The alkyl esters are prepared by heating the protected or unprotected carboxylic acids in a desired alkanol, preferably methanol, in the presence of an acid catalyst recited above. Purification via standard means such as distillation, column chromatography, or recrystallization affords the desired alkyl ester derivative.

The esterification of steroid alcohol 1 with either A—CH(OH)CO2H, A—CH(OP)CO2H, (HO)C$_6$H$_4$CO$_2$H or (PO)C$_6$H$_4$CO$_2$H, or an alkylester derivative thereof, is preferably conducted in the presence of a reaction solvent including, but not limited to methylene chloride, chloroform, carbon tetrachloride, benzene, toluene, xylenes, tetrahydrofuran, diethyl ether, other suitable solvents known to those skilled in the art, and mixtures thereof. Preferably, the reaction solvent is toluene.

The protected or unprotected carboxylic acids may also be converted to their acid halide derivatives, preferably acid chloride derivatives, prior to esterification with 1. Preferably, the carboxylic acid is protected. The protected or unprotected carboxylic acids may be treated with either thionyl chloride or oxallyl chloride to give the corresponding acid chlorides, which may then react with 1 to give esters 2 and 3 respectively. Such an esterification is generally performed in an organic solvent including, but not limited to methylene chloride, chloroform, carbon tetrachloride, benzene, toluene, xylenes, tetrahydrofuran, diethyl ether, other aprotic organic solvents known to those skilled in the art, and mixtures thereof. The esterification is preferably performed in the presence of a base including, but not limited to triethylamine, disopropylethylamine, pyridine, 4-dimethylaminopyridine, other bases known to those skilled in the art, and mixtures thereof. If 1 and the protected or unprotected carboxylic acids are soluble in the base, the organic solvent may optionally be omitted.

In addition, steroid alcohol 1 may be esterified by either the protected or unprotected carboxylic acids in the presence of dicyclohexylcarbodiimide. Preferably, a protected carboxylic acid is used. Such a reaction is generally performed in an organic solvent as described above.

After the esterification of 1 with either A—CH(OP)CO$_2$H or POC$_6$H$_4$CO$_2$H, the protecting group is removed to give esters 2 or 3, respectively. Methods for removing the protecting group can be found in T. W. Greene, *Protective Groups in Organic Synthesis*, John Wiley & Sons, New York, 1981.

The compound of formula III (DHEA salicylate) can be synthesized according to two routes shown below.

In the first route (Scheme 2), DHEA is transesterified with an alkyl salicylate to give DHEA salicylate. Such alkyl salicylates contemplated by the present invention are C$_1$–C$_5$ alkyl salicylates. Preferably, the alkyl salicylate is methyl salicylate. An excess of either reactant, preferably an excess of alkyl salicylate, is used to effect transesterification. DHEA and the alkyl salicylate, preferably methyl salicylate, are heated together, optionally in the presence of a suitable solvent such as those described above or known by those of ordinary skill in the art to facilitate such transesterification reactions, at temperatures ranging from about 25° C. to about 120° C., preferably from about 45° C. to about 85° C., to give DHEA and an alkanol. It will be understood by those of ordinary skill in the art that the alkanol obtained as a by-product of transesterification corresponds to the alkyl salicylate employed in the transesterification reaction. If methyl salicylate is used, the alkanol is methanol. The alkanol by-product may be distilled away from the reaction mixture, which further drives the reaction to completion.

In addition, the transesterification reaction may optionally proceed in the presence of a suitable catalyst. Suitable catalysts can be either acid catalysts or base catalysts. Such acid catalysts include, but are not limited to, hydrochloric acid, sulfuric acid, p-toluenesulonic acid, methanesulfonic acid, and other acid catalysts known to those skilled in the art. Such base catalysts include, but are not limited to the alkali metal hydroxides, alkaline earth hydroxides, alkoxide salts such as titanium isopropoxide and others known to those skilled in the art.

The DHEA salicylate product may optionally be purified by methods such as recrystallization or column chromatography. Such purification may be used to remove from the reaction mixture unwanted byproducts of transesterification, such as, for example, salicylsalicylic acid or disalicylide, and unreacted starting material.

Scheme 2

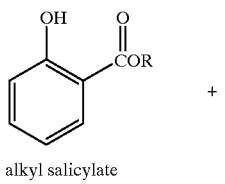

alkyl salicylate

+

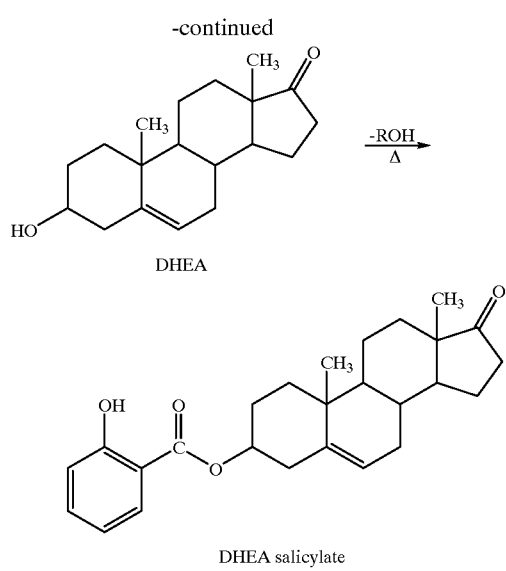

In the second route (Scheme 3), salicylic acid, optionally an O-protected derivative thereof, is treated with an acid halide-forming reagent such as thionyl chloride or oxallyl chloride to give a salicylyl halide, or if an O-protected derivative of salicylic acid is used, an O-protected salicylyl halide, which reacts with DHEA to give DHEA salicylate or if an O-protected derivative of salicylyl chloride is used, O-protected DHEA. Suitable O-protecting groups useful for protecting the hydroxyl group of salicylic acid are found in T. W. Greene, *Protecting Groups in Organic Synthesis*, John Wiley & Sons, New York, 1981. Preferably, the acid halide-forming reagent is thionyl chloride and the salicylyl halide is salicylyl chloride. The reaction may optionally be performed in an aprotic solvent such as methylene chloride, chloroform, carbontetrachloride, tetrahydrofuran, 1,4-dioxane, benzene, toluene, xylenes, hexane, or preferably, cyclohexane. Preferably, a reaction catalyst, such as dimethylformamide, is added to the mixture. If a reaction solvent is used, the mixture of reaction solvent, salicylic acid or its O-protected derivative, and acid halide-forming reagent, preferably in the presence of a reaction catalyst, is heated from about 25° C. to reflux temperatures from about 1 hour to approximately overnight, preferably from about 1 hour to about several hours.

The reaction mixture is then concentrated, optionally in vacuo, to afford acid chloride product, which can be used without further purification or optionally purified via recrystallization prior to use.

Alternatively, the reaction mixture is diluted with an aprotic solvent, such as any of those listed above, to provide a solution containing the acid chloride product. If salicylic acid is used in the acid chloride-forming reaction, the above solution may also contain salicylsalicylic acid, disalicylide, or other salicylic acid-derived byproducts formed during the reaction between salicylic acid and the acid halide-forming reagent.

The crude or purified acid chloride product, or the solution containing the acid chloride product is then combined with DHEA, optionally a solution of DHEA in an aprotic solvent, such as any of those listed above, to give DHEA salicylate, or if an O-protected derivative of salicylyl chloride is used in the reaction, and O-protected derivative of DHEA. The esterification can proceed at temperatures ranging from about −78° C. to 150° C., preferably from about 0°

C. to about 100° C. and most preferably from about 25° C. to about 85° C. The esterification reaction can optionally proceed in the presence of a base such as triethylamine, diisopropyl ethyl amine, pyridine, 4-dimethylaminopyridine, or mixtures thereof. If base is added to the reaction mixture, it may be present in the amount of 0.01–10 eq., preferably 0.01–2 eq. relative to the limiting reagent (i.e., either the DHEA or salicylyl halide which is not used in excess).

The reaction mixture, which contains the DHEA salicylate product or its O-protected derivative and optionally salicylsalicylic acid, disalicylide or other salicylic acid-derived byproducts, is purified by standard techniques, such as recrystallization or column chromatography, to give substantially pure DHEA salicylate or its O-protected derivative. Removal of the O-protecting group of O-protected DHEA provides DHEA. Methods for the removal of the chosen O-protecting group are found in T. W. Greene, *Protecting Groups in Organic Synthesis*, John Wiley & Sons, New York, 1981.

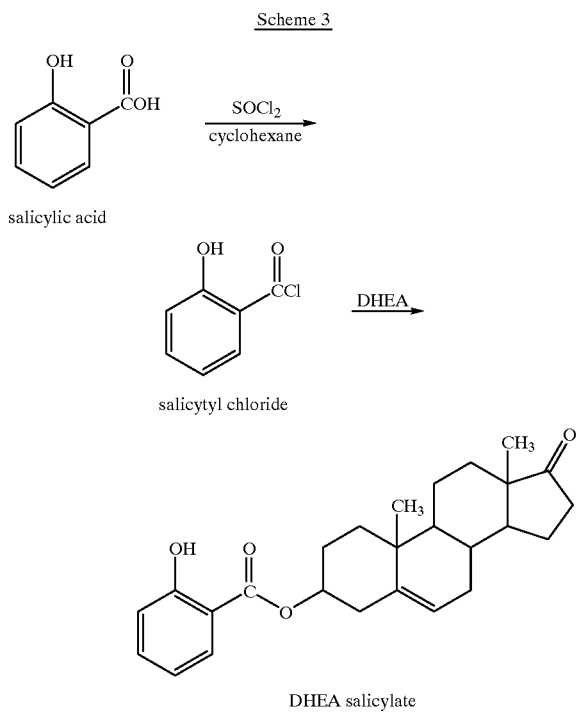

Scheme 3

4.3. Compositions

The compositions of the present invention can be used to treat skin atrophy and other disorders including but not limited to dry skin, dandruff, acne, keratoses, psoriasis, eczema, pruritis, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers.

In regulating skin atrophy or other skin disorders as described above, compositions containing 0.005–50 wt. %, preferably 0.01–25 wt. % and most preferably 0.01–5 wt. % of the steroid ester can be employed. It should be understood that two or more steroid esters of the present invention can be used in combination such that the combined weight % of those esters used in the above-mentioned compositions is within those ranges mentioned above. Such compositions are preferably to be applied topically, so as to minimize systemic effects or undesirable side effects. The novel compounds may also be employed in pharmaceutical compositions suitable for parenteral (including subcutaneous, transdermal, intramuscular and intravenous) administration, although the most suitable route in any case will depend on the nature and severity of the condition being treated. The most preferred mode of administration for treating skin disorders, in particular skin atrophy or the skin disorders described above, is topical. In addition, the novel compounds of the present invention may be further employed in cosmetic compositions. In such an instance, the preferred mode of administration for treating skin disorders, in particular skin atrophy, is topical.

The compounds of the present invention can be formulated into suitable cosmetic or pharmaceutical compositions depending on the particular use for which it is to be intended, for example, cosmetic or therapeutic, or both. The cosmetic compositions can comprise one or more of the steroid esters of formula II and a pharmaceutically or dermatologically acceptable carrier or excipient.

The compositions of the present invention useful for topical application may contain additional ingredients such as carrier, excipient or vehicle ingredients such as, for example, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments which are non-toxic and pharmaceutically or dermatologically acceptable. Additionally, moisturizers or humectants can be added to the present compositions if desired. Examples of such additional ingredients can be found in *Remington's Pharmaceutical Sciences*, Eighteenth Edition, A. R. Gennaro, Ed., Mack Publishing Co., Easton, Pa., 1990.

In addition to these and other vehicles which will be obvious to those of ordinary skill in the art, it will be understood that the pharmaceutical or cosmetic compositions of the present invention may include other ingredients such as those that improve or eradicate age spots, keratoses and wrinkles; analgesics; anesthetics; antiacne agents; antibacterials; antiyeast agents; antifungal agents; antiviral agents; antidandruff agents; antidermatitis agents; antipruritic agents; antiemetics; antimotion sickness agents; antiinflammatory agents; antihyperkeratolytic agents; antidryskin agents; antiperspirants; antipsoriatic agents; antieborrheic agents; hair conditioners and hair treatment agents; antiaging antiwrinkle agents; antiasthmatic agents and bronchodilators; sunscreen agents; antihistamine agents; skin lightening agents; depigmenting agents; vitamins; corticosteroids; tanning agents; hormones; retinoids; topical cardiovascular agents; clotrimazole; ketoconazole; miconazole; griseofulvin; hydroxyzine; diphenhydramine; pramoxine; lidocaine; procaine; mepivacaine; monobenzone; erythidocaine; procaine; mepivacaine; monobenzone; erythromycin; tetracycline; clindamycin; meclocyline; hydroquinone; minocycline; naproxen; ibuprofen; theophylline; cromolyn; albuterol; retinoic acid; 13-cis retinoic acid; hydrocortisone; hydrocortisone 21-acetate; hydro-cortisone 17-valerate; hydrocortisone 17-butyrate; betamethasone valerate; betamethasone dipropionate; triamcinolone acetonide; fluocinonide; clobetasol propionate; benzoyl peroxide; crotamiton; propranolol; promethazine; vitamin A palmitate; vitamin E acetate and mixtures thereof.

The compounds of the present invention can be used as their pharmaceutically or cosmetically acceptable salts. Such salts include, but are not limited to, sodium, potassium, lithium, calcium, magnesium, iron and zinc salts.

4.4. Methods for Regulating Skin Atrophy

The present invention also relates to a method for regulating skin atrophy or other skin disorders including but not limited to dry skin, dandruff, acne, keratoses, psoriasis, eczema, pruritis, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers. Such a method comprises applying to the skin a safe and effective amount of one or more of the novel steroid esters of the present invention. While the present invention relates to novel steroid esters used to treat skin disorders, the present invention further relates to the use of compositions, such as those discussed above, comprising one or more of said steroid esters, to be used for treating skin disorders. The amount of steroid ester and frequency of treatment will vary widely depending upon the level of skin atrophy already in existence in the subject (if such exists), the rate of further atrophy, and the level of regulation desired.

A preferred method of treating the skin is via chronic topical application of a safe and effective amount of the steroid ester to regulate skin atrophy to treat other skin maladies described above. The amount of steroid ester and frequency of topical application to the skin can vary widely, depending upon the particular skin disorder and the severity thereof. It is well within the purview of the skilled artisan, such as a dermatologist or other health care provider, to regulate dosages according to patient needs. It is suggested as an example that topical application range from about once per week to about 4 or 5 times daily, preferably from about 3 times a week to about 3 times daily, most preferably about once or twice per day. The composition for topical application will comprise from about 0.005% to about 50%, preferably from about 0.01% to about 25%, most preferably from about 0.01% to about 5% of the active compound or mixture of compounds. By "chronic" application, it is meant herein that the period of topical application may be over the lifetime of the patient, preferably for a period of at least about one month, more preferably from about three months to about twenty years, more preferably from about six months to about ten years, more preferably still from about one year to about five years, thereby resulting in regulation of skin atrophy or other skin maladies described above.

A further preferred method of treating the skin is via occasional topical application of a safe and effective amount of the steroid ester for cosmetic use. Such cosmetic uses include but are not limited to moisturizing skin; masking skin blemishes or other undesired attributes; highlighting the skin as, for example, an eye shadow; improving skin texture; and the like. The amount of steroid ester and frequency of topical application to the skin can vary widely, depending upon desirability of use. The composition for topical application will comprise from about 0.005% to about 50%, preferably from about 0.01% to about 25%, most preferably from about 0.01% to about 5% of the active compound or mixture of compounds.

In another embodiment of the invention, regulating skin atrophy or treating other skin maladies described above involves applying both a safe and effective amount of the steroid ester(s) and a safe and effective amount of one or more of a sunscreening agent, an anti-inflammatory agent, an anti-oxidant/radical scavenging agent, a chelating agent, a retinoid and/or a benz-ofuran derivative to the skin simultaneously. As used herein, "simultaneous application" or "simultaneously" means applying the agents to the skin at the same situs on the body at about the same time. Though this can be accomplished by applying the agents separately to the skin, preferably a composition comprising all the desired agents commingled is applied to the skin. The amount of sunscreening agent applied is generally from about 0.02 mg to about 1.0 mg per $cm^2$ skin. The amount of anti-inflammatory agent applied is generally from about 0.005 mg to about 0.5 mg, preferably from about 0.01 mg to about 0.1 mg per $cm^2$ skin. The amount of chelating agent generally applied is from about 0.001 mg to about 1.0 mg, preferably from about 0.01 mg to about 0.5 mg, more preferably from about 0.05 mg to about 0.1 mg per $cm^2$ skin. The amount of retinoid applied is generally from bout 0.00001 mg to about 0.02 mg per $cm^2$ skin. The amount of benzofuran derivative applied is generally from about 0.001 mg to about 1.0 mg/$cm^2$ skin per application, preferably from about 0.01 to about 0.5 mg/$cm^2$ skin per application. The amount of steroid ester(s) applied is generally from about 0.001 mg to about 1.0 mg per $cm^2$ skin per application, preferably from about 0.01 mg to about 0.5 mg per $cm^2$, more preferably from about 0.05 to about 0.25 mg/$cm^2$ skin per application, which may vary upon the severity of the condition to be treated and the efficacy of the compounds employed.

The following specific, non-limiting examples concern the synthesis of the steroid esters of the instant invention and the preparation of a topical lotion, topical cream, topical ointment and topical gel using vehicles previously used in other preparations. The formulations for these preparations are given below in Table 1.

EXAMPLE NO. 1a

Dehydroepiandrosteryl Salicylate (DHEA Salicylate).

To 100 g of DHEA in 500 ml of methylene chloride are added 1.2 eq. of pyridine followed by 1.1 eq. of 2-acetoxybenzoyl chloride and catalytic 4-dimethylaminopyridine. The reaction is heated at 80° C. for 2 h. After cooling to room temperature, the reaction mixture is washed with 1N HCl to remove excessive pyridine, and the organic phase is dried ($MgSO_4$), filtered and concentrated in vacuo. The residue is dissolved in methanol/water and treated with excess sodium bicarbonate to give the title compound.

EXAMPLE NO. 1b

Dehydroepiandrosteryl Salicylate (DHEA Salicylate).

To a reaction vessel fitted with a distillation head is added loog of DHEA, 5.0 eq of methyl salicylate and 0.01–0.05 eq. of p-toluenesulfonic acid. The reaction mixture is heated at 80–100° C. until methanol ceases to distill off. The remaining methyl salicylate is removed via distillation under reduced pressure. The residue is purified via recrystallization or column chromatography to afford the title compound.

EXAMPLE NO. 2

Butylene glycol and water are mixed and dissolved in alcohol. The resultant vehicle mixture and DHEA salicylate of Example No. 1 are mixed and dissolved. The resultant formulation is a tincture.

EXAMPLE NO. 3

In this example a topical cream is prepared by first mixing and melting squalane, stearyl alcohol NF, cetyl alcohol polyethylene glycol cetyl ether, mineral oil NF and petroleum USP, at 70° C. A second mixture is formed by mixing and dissolving methyl paraben NF and propyl paraben NF in water, at 70° C. The second mixture is slowly added to and mixed with the first mixture to form an emulsion. DHEA salicylate of Example No. 1 is dispersed in the resultant emulsion at 50° C. The resultant composition is slowly cooled with mixing until the composition reaches room temperatures.

EXAMPLE NO. 4

In this example a topical ointment is prepared. As a first step, glyceryl monostearate is mixed and melted in petrolatum USP at 70° C. As a second step, DHEA salicylate of Example No. 1 is mixed and dissolved in butylene glycol at 70° C. The resultant composition of step 2 is slowly added to the resultant composition of step 1, with mixing. This mixture is then cooled to its congealing point with mixing and then cooled to room temperature without mixing.

EXAMPLE NO. 5

In this example a topical gel is prepared. As a first step, hydroxy propyl cellulose is hydrated and dissolved into water. As a second step, DHEA salicylate of Example No. 1, butylene glycol and PPG-12-Buteth-16 are dissolved in alcohol. Slowly the resultant mixture of step 2 is added into the resultant mixture of step 1 with mixing until a gel forms.

TABLE 1

Steroid Ester Formulations

| Ingredients | Example No. 2 Topical Tincture % w/w | Example No. 3 Topical Cream/ Lotion % w/w | Example No. 4 Topical Ointment % w/w | Example No. 5 Topical Gel % w/w |
|---|---|---|---|---|
| 1. Steroid ester of formula I or DHEA Salicylate | 1.0 | 1.0 | 1.0 | 1.0 |
| 2. Methyl Paraben NF | | .01 | | |
| 3. Propyl Paraben NF | | .01 | | |
| 4. Hydroxy Propyl Cellulose (note 1) | | | | 1.0 |
| 5. PPG-12-Buteth-16 (note 2) | | | | 2.0 |
| 6. Squalane (note 3) | | 2.0 | | |
| 7. Glyceryl Monostearate NF | | | 2.0 | |
| 8. Stearyl Alcohol NF | | 2.8 | | |
| 9. Cetyl Alcohol NF | | 4.2 | | |
| 10. Polyethylene Glycol Cetyl Ether (note 4) | | 5.0 | | |
| 11. Mineral Oil NF | | 5.0 | | |
| 12. Butylene Glycol | 4.0 | | 12.0 | 4.0 |
| 13. Petrolatum USP | | 5.4 | 85.0 | |
| 14. Alcohol (note 5) | 89.0 | | | 47.0 |
| 15. Water | 6.0 | 74.4 | | 45.0 |
| | 100.0 | 100.0 | 100.0 | 100.0 |

Notes:
(1) available under the trademark Klucel ® from Hercules
(2) available under the trademark Ucon ® fluid 50 HB from Union Carbide
(3) available under the trademark Robane ® from Robeco
(4) available under the trademark Brij 58 ® from ICI
(5) contains 95% ethanol and 5% water

EXAMPLE NO. 6

To examine the effect of the steroid esters of the present invention on stratum corneum, stratum corneum samples are first equilibrated to 44% relative humidity (RH) by suspending the samples over a saturated salt solution of potassium carbonate. After equilibration, the stratum corneum samples are extended by 2% of their original length at 20 mm/min using a linear extensometer. The amount of force required to extend the sample is computed and the information displayed as a force extension graph on a personal computer. The initial slope of the curve in the Hookean region is then used as an indicator of the integrity of the stratum corneum (gram-force/100% extension). 50 $\mu$l of the steroid ester to be tested is then applied to the external surface of five pieces of stratum corneum samples and rubbed in with 20 strokes of a gloved finger. The samples are then equilibrated to 80% RH by suspending over a saturated salt solution of ammonium sulfate in humidity chambers and then incubated at this humidity for three hours. The samples are then reequilibrated to 44% RH and after conditioning, restretched to 2% extension. Results are then expressed as extensibility ratios of before/after treatment. The same test is run for 4% extension.

EXAMPLE NO. 7

To the half an area of the face, neck, forearm, back or buttocks of each member of a panel of approximately 50 healthy volunteers is applied a composition comprising 0.01–5 wt. % of a steroid ester or mixture of steroid esters of the present invention and to the other half an area is applied a control composition. Applications are made once to 4 times daily for up to six months or more depending upon the condition to be treated. Panelists are assessed by expert assessors for overall improvement in the condition to be treated or the look and feel of the skin.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A compound of formula II:

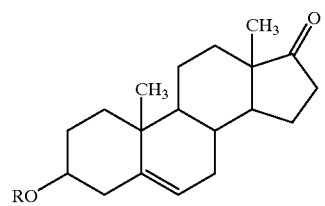

or pharmaceutically or cosmetically acceptable salts thereof, wherein:

R is A—CH(OH)—C(O)—; and

A is hydrogen or a $C_1$–$C_{22}$ alkyl or alkenyl group, said $C_1$–$C_{22}$ alkyl or alkenyl group being optionally substituted with one or more $C_1$–$C_4$ alkyl groups, phenyls, halogens or hydroxyl groups, said phenyl being optionally substituted with one or more halogens, hydroxyl groups or methoxyl groups.

2. The compound of claim 1, wherein R is selected from the group consisting of 2-hydroxyethanoyl; 2-hydroxypropanoyl; 2-methyl-2-hydroxypropanoyl; 2-hydroxybutanoyl; 2-hydroxypentanoyl; 2-hydroxynonanoyl; 2-hydroxydecanoyl;

2-hydroxyoctanoyl; 2-hydroxydodecanoyl; 2-hydroxytetradecanoyl; 2-hydroxyhexadecanoyl; 2-hydroxyoctadecanoyl; 2-hydroxyeicosanoyl; 2-hydroxyphenyl-2-hydroxyethanoyl; 2,2-diphenyl-2-hydroxyethanoyl; 3-phenyl-2-hydroxypropanoyl; 2-phenyl-2-methyl-2-hydroxyethanoyl; 2-(4'-chlorophenyl)-2-hydroxyethanoyl; 2-(4'-hydroxy-3'methoxyphenyl)-2-hydroxyethanoyl; 3-(2'-hydroxyphenyl)-2-hydroxypropanoyl; 3-(4'-hydroxyphenyl)-2-hydroxypropanoyl; and 2-(3',4'-dihydroxyphenyl)-2-hydroxyethanoyl.

3. A composition for regulating skin atrophy, said composition comprising a pharmaceutically or cosmetically acceptable vehicle and a compound of claim 1.

4. The composition of claim 3 wherein said compound is present in an amount of about 0.01–5 wt. % of the composition.

5. The composition of claim 3 wherein said vehicle is selected from the group consisting of lotions, tinctures, creams, emulsions, gels and ointments.

6. The composition of claim 3 wherein said composition is a topical composition.

7. A method for regulating skin atrophy in a patient which comprises topically administering to the area of atrophied skin in the patient a composition comprising a pharmaceutically or cosmetically acceptable vehicle and a compound of claim 1.

8. A method for treating a skin disorder in a patient which comprises topically administering to the area of the skin to be treated in the patient a composition comprising a pharmaceutically or cosmetically acceptable vehicle and a compound of claim 1, said skin disorder selected from the group consisting of dry skin, dandruff, acne, keratoses, psoriasis, eczema, pruritis, age spots, lentigines, melasmas, wrinkles, warts, blemished skin, hyperpigmented skin, hyperkeratotic skin, inflammatory dermatoses, age-related skin changes and skin in need of cleansers.

9. The method of claim 7 wherein said compound is present in an amount of about 0.01–5 wt. % of the composition.

10. The method of claim 8 wherein said compound is present in an amount of about 0.01–5 wt. % of the composition.

11. The method of claim 7 wherein said vehicle is selected from the group consisting of lotions, tinctures, reams, emulsions, gels and ointments.

12. The method of claim 8 wherein said vehicle is selected from the group consisting of lotions, tinctures, creams, emulsions, gels and ointments.

* * * * *

UNITED STATES PATENT AND TRADEMARK OFFICE
CERTIFICATE OF CORRECTION

PATENT NO.  : 6,284,750 B1
DATED       : September 4, 2001
INVENTOR(S) : Gubernick et al.

It is certified that error appears in the above-identified patent and that said Letters Patent is hereby corrected as shown below:

Column 16, claim 11,
Line 2, thereof, please replace "reams" with -- creams --.

Signed and Sealed this

Twelfth Day of March, 2002

Attest:

JAMES E. ROGAN
*Director of the United States Patent and Trademark Office*

*Attesting Officer*